United States Patent
Lidman et al.

(10) Patent No.: US 6,611,711 B1
(45) Date of Patent: Aug. 26, 2003

(54) IMPLANTABLE CARDIAC STIMULATION DEVICE WITH PARAMETER CONTROL

(75) Inventors: Johan Lidman, Stockholm (SE); Jonas Andersson, Johanneshov (SE); Sven-Erik Hedberg, Kungsängen (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/807,803

(22) PCT Filed: Sep. 14, 1999

(86) PCT No.: PCT/SE99/01603

§ 371 (c)(1),
(2), (4) Date: Aug. 27, 2001

(87) PCT Pub. No.: WO00/23145

PCT Pub. Date: Apr. 27, 2000

(30) Foreign Application Priority Data

Oct. 20, 1998 (SE) .............................................. 9803581

(51) Int. Cl.[7] ............................................. A61N 1/362
(52) U.S. Cl. ................................ 607/9; 607/59; 607/63
(58) Field of Search ................................ 607/9, 17, 27, 607/30, 31, 59, 62, 63

(56) References Cited

U.S. PATENT DOCUMENTS

| | | | | |
|---|---|---|---|---|
| 4,432,360 A | * | 2/1984 | Mumford et al. | 607/30 |
| 4,467,810 A | | 8/1984 | Vollmann | |
| 5,653,735 A | | 8/1997 | Chen et al. | |
| 5,749,907 A | * | 5/1998 | Mann | 607/27 |
| 6,014,587 A | * | 1/2000 | Shaw et al. | 607/45 |
| 6,073,049 A | * | 6/2000 | Alt et al. | 607/31 |
| 6,289,248 B1 | * | 9/2001 | Conley et al. | 607/59 |

FOREIGN PATENT DOCUMENTS

EP 0 147 820 7/1985

* cited by examiner

Primary Examiner—Kennedy Schaetzle
(74) Attorney, Agent, or Firm—Schiff Hardin & Waite (57) ABSTRACT

An implantable cardiac stimulation device operates according to a first pacing algorithm executable by a microprocessor and which is able to independently perform stimulation therapy for a patient's heart, as well as according to a second pacing algorithm which is also microprocessor-executable. The first and second algorithms actively generate stimulation parameters during each cardiac cycle, but the stimulation parameters generated by the second algorithm are only permitted to result in actual stimulation therapy if those parameters fall within parameter ranges that are calculated to be allowable for stimulation by the first algorithm.

11 Claims, 6 Drawing Sheets

IMPLANTABLE CARDIAC STIMULATION DEVICE WITH PARAMETER CONTROL

BACKGROUND OF THE INVENTION

1. Field of the Invention

The present invention is directed to an implantable cardiac stimulation device of the type which is operable in multiple modes respectively based on different algorithms.

2. Description of the Prior Art

Implantable cardiac stimulation systems generally include one or more stimulation and sensing electrodes, arranged on one or many insulated electrode leads, and a pacemaker housing having inter alia, a control unit and pulse generating means.

The one or more electrodes are used to provide electrical stimuli directly to the heart muscle. These stimuli can be pacing pulses, and can sometimes include relatively larger shocks, such as are used to break up tachyarrhythmias. The electrodes may also be used for sensing the intracardial electrogram (IEGM). In addition to these electrodes, and to further enhance the pacemaker therapy, sensors may be used by the device to sense blood gases, respiration, cardiovolume, temperature, pressure or other physiological conditions.

The pacemaker housing is normally implanted subcutaneously in the region of the clavicle. The insulated electrode lead or leads are inserted into the heart in accordance with the normal procedure that is well known to those skilled in the field of pacemakers and are then connected to the housing.

The control units of modem devices are sophisticated and include control logic circuits, timing circuits, and input/output (I/O) circuitry that connects the control logic with the electrodes and/or sensors. For example, the I/O circuit provides analog-to-digital and digital-to-analog conversion, and provides the desired electrical stimuli as pulses of the desired amplitude, duration and frequency. The control unit typically includes a microprocessor and memory, and is also configured to allow remote programming after implantation in the patient's body.

Early pacemakers were fixed-rate devices providing electrical stimuli to the heart if the heart failed to beat within a predetermined time period. However, microprocessor-based technology has enabled implantable devices to make complex logical decisions based on a variety of physiological data. As examples, modem implantable devices have the ability to distinguish between different types of tachyarrhythmia and to select an appropriate therapy that does not impose undesired trauma on the heart. The present day microprocessor-based devices are capable of distinguishing normal physiological conditions from pathological conditions and also of selecting between alternative therapies for the latter. Logical decisions based on physiological variables, therapies responsive to different heart conditions, and automatic self-configuration are examples of what is referred to as automaticity.

As the pacing algorithms grow more sophisticated and complex the algorithm code itself will also grow in size and complexity and thus require a high degree of operational safety.

U.S. Pat. No. 5,633,735 assigned to Pacesetter, Inc., discloses a device capable of operation in three different modes. The device is capable of detecting software errors and in the case of such detection switches from the first mode to the second mode of operation. Each of the first and second modes is able to function automatically. If another software error is detected the device switches to the third mode which is fixed-rate pacing. The device is not capable of switching back to the first or second mode. The error-detecting mechanism can detect software-errors such as parity error, watchdog error, checksum error etc.

U.S. Pat. No. 4,467,810 discloses a multi-mode microprocessor-based programmable cardiac pacemaker.

Software algorithms supporting new additional pacing functions must be able to cooperate with a basic or existing algorithm in a safe and reliable way.

Accordingly, there is a definite need for an implantable device, which is capable of supporting new pacing algorithms, as well as being functional as a well-established and well-tested pacemaker.

SUMMARY OF THE INVENTION

An object of the invention is to provide an implantable cardiac stimulation device offering a high degree of safety for a microprocessor-based device having two or more pacing algorithms.

The above object is achieved in accordance with the principles of the present invention in an implantable cardiac stimulation device having a first pacing algorithm which is executable by a microprocessor and which is capable of independently administering stimulation therapy to a patient's heart, and wherein a second microprocessor-executable pacing algorithm is provided, the first and second pacing algorithms both actively generating pacing parameters during each cardiac cycle, and wherein the pacing parameters of the second pacing algorithm are only able to result in an actually-administered stimulation therapy if these parameters fall within parameter ranges which are calculated to be allowable for stimulation by the first pacing algorithm.

Thus, improved safety is obtained by allowing two or more pacing algorithms, including a first algorithm, during each heart cycle to actively generate pacing parameters, but only allowing a request for stimulation therapy from one of the other algorithms if this request falls within parameter ranges calculated to be allowable for stimulation by the first algorithm.

A pacing algorithm is in this context regarded as a set of instructions capable of performing stimulation therapy by generating instructions to pulse generating circuits.

DESCRIPTION OF THE PREFERRED EMBODIMENTS

Figure 1:
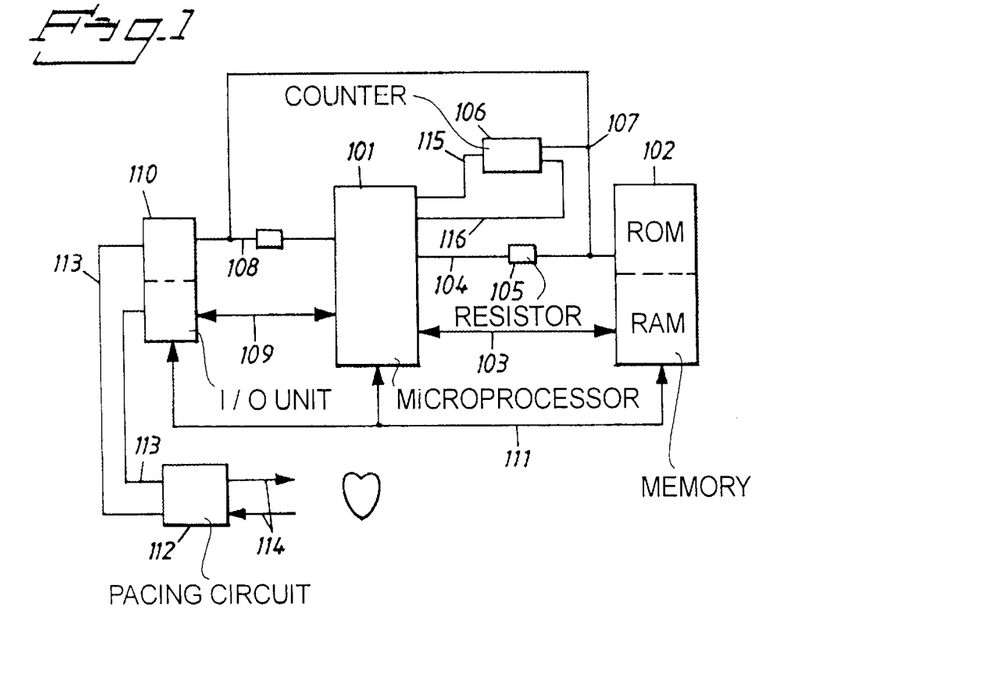
FIG. 1 is a block diagram of a first preferred embodiment of the invention.

FIG. 1 shows a schematic block diagram according to a first preferred embodiment of the invention. This embodiment uses a microprocessor, which does not have hardware support for a user and supervisor mode. This is the type of processor used in modern pacemakers and can be for example a Rockwell 6502, Motorola 65C11 or Motorola 65C05 processor.

A microprocessor is denoted 101 and a memory is denoted 102. The memory 102 contains both a read-only memory (ROM) and a random access memory (RAM). The microprocessor 101 has a 16-bit address-bus with the first 15-bits denoted 103 and the $16^{th}$ address-bit denoted 104. A resistor 105 is arranged in the $16^{th}$ address-bit line so that a counter 106 may block the corresponding part of the memory 102 for the microprocessor 101 through a first connection 107, even if the $16^{th}$ address-bit is used by the executive code in the microprocessor. In a similar manner, the first connection 107 is connected to a $4^{th}$ address-bit 108 of a 4-bit address-bus, with the first 3-bits denoted 109, to an input/output (I/O) unit 110.

A data-bus is denoted 111 and a pacing circuit for delivering electrical stimulation to the heart and also for retrieving data representing physiological or physical information, is denoted 112. Examples of physiological data can be for instance the IEGM or the blood pressure, and an example of a physical information could be for instance measurement of acceleration.

The I/O unit 110 is, in this embodiment, connected to the pacing circuit 112 through connection 113. The pacing circuit 112 and the I/O unit 110 may, in another embodiment, be integrated. The pacing circuit 112 is further connected to the heart via electrode leads 114. One or more leads 114 may be used and they may deliver electrical stimulation to the heart as well as sense various physiological parameters.

The 4th-bit 108 of the I/O-bus controls the output to the pacing circuit 112. A second connection 115 enables the microprocessor 101 to set and start the counter 106, and a third connection 116 enables the counter 106 to deliver an interrupt to the microprocessor 101.

Figure 2:
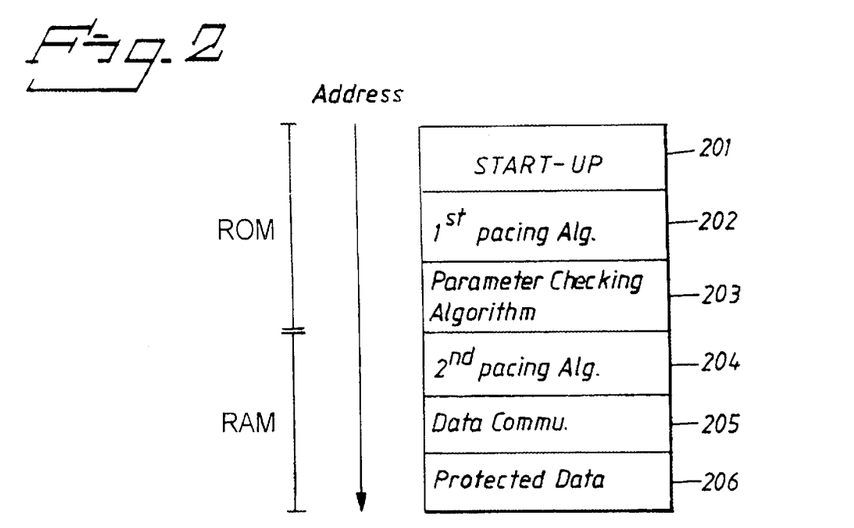
FIG. 2 shows a memory layout for the first embodiment of the invention.

FIG. 2 shows layout of the memory 102 in more detail. At the lowest part of the memory is a start-up program 201. A first pacing algorithm 202 includes a parameter checking algorithm 203. The start-up program 201, the first pacing algorithm 202 and the parameter checking algorithm are all located in the read-only-memory ROM. The first pacing algorithm is a reliable and safe pacing algorithm. It may or may not contain automaticity features and may be very complex.

The start-up program 201 is the first code that is executed when the pacemaker is first started or restarted. The startup program 201 sets the counter 106. The counter blocks the 16th-bit of the memory address-bus, and thus the upper part of the memory 102, and the $4^{th}$-bit of the I/O-buss, and thus the output to the pacing circuit 112, and starts counting down to zero. The start-up program 201 then jumps to a second pacing algorithm 204. The second pacing algorithm 204 can be an advanced pacing algorithm that supports the use of data detected by physiological sensors, involves various changes of the mode of operation for the stimulation device or enables the stimulation device to detect various heart diseases, e.g. ischemia.

The second pacing algorithm 204 executes and stores pacing parameters in a data communication area 205. When the second pacing algorithm is finished it goes into sleep mode. A protected memory area is denoted 206. Since the counter 106 blocks the upper part of the memory area 206, the second algorithm 204 may not store data in the protected area 206. The second pacing algorithm 204 cannot provide access by the I/O unit 110 to the first pacing algorithm 202 since also this is blocked by the counter 106. It is, however, possible for the second pacing algorithm 204 to read data through input unit 110 since the input unit 110 is controlled by the three least significant bits 109 in the I/O-bus which are not blocked by the counter 106. Thus the second pacing algorithm 204 can read physiological data which might be important for the second pacing algorithm 204.

Figure 3:
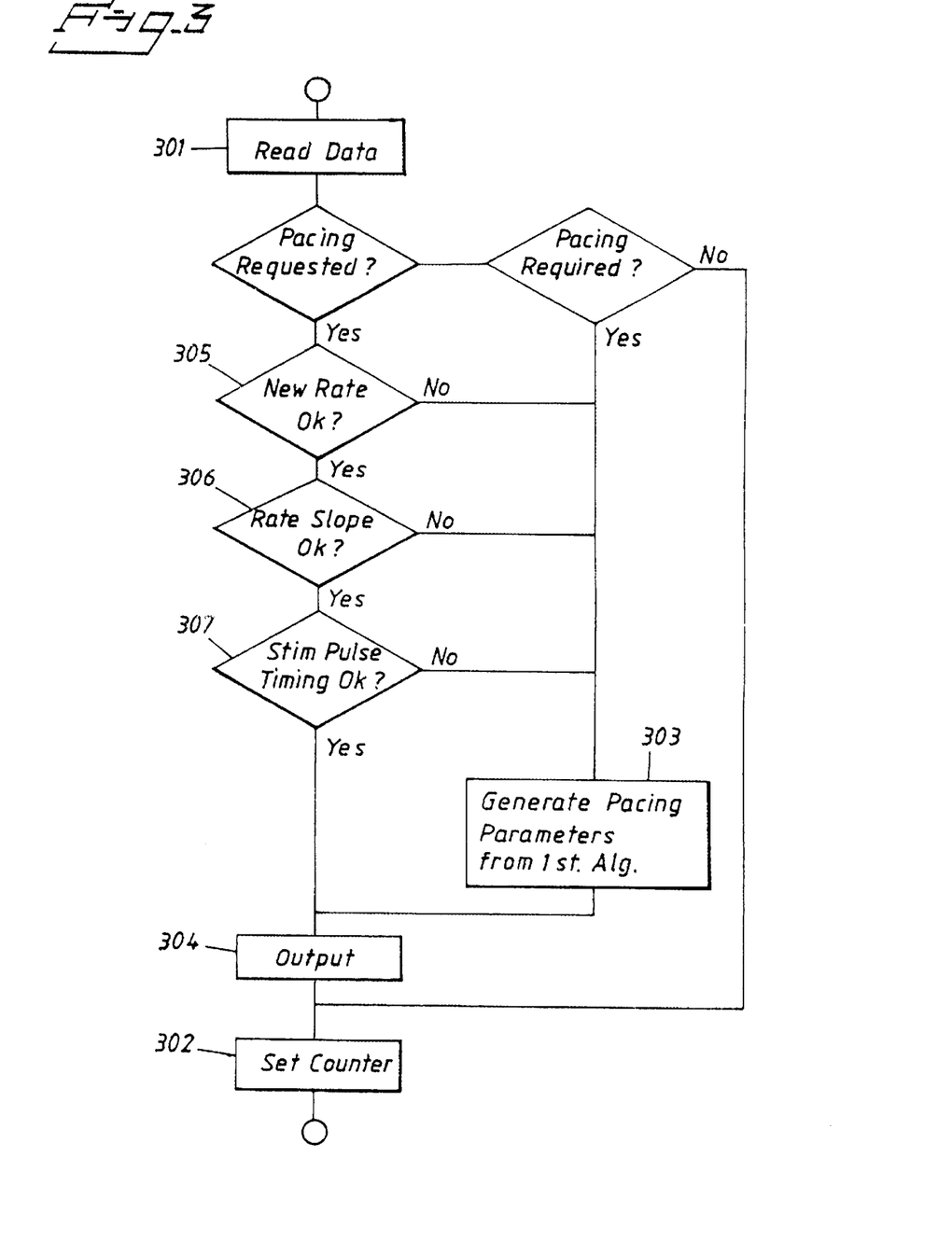
FIG. 3 is a flowchart for a parameter checking algorithm according to the first embodiment of the invention.

When the counter 106 reaches zero it releases the upper protected memory 206 and the output I/O unit 110 and generates an interrupt to the microprocessor 101. The microprocessor 101 jumps to the parameter checking algorithm 203 upon the request of this interrupt. FIG. 3 shows a flow chart of the parameter checking algorithm 203. The checking algorithm 203 reads the data 301 that the second pacing algorithm 204 has stored in the data communication area 205.

Several options exist for ensuring that the data supplied by the second pacing algorithm 204 is safe, e.g. by interruption of the interrupt requested by the counter 106. It should for instance not be possible for the second pacing algorithm 204 to store only one part of the data and then be interrupted.

One way of achieving this is to use one bit in the data communication area as a flag indicating that the second pacing algorithm 204 has finished storing safe data in the data communication area. This bit is then checked by the parameter checking algorithm 203, and if the flag is set the data in the data communication area 205 are assumed to be okay. The checking algorithm 203 then resets the bit.

If pacing is not requested and pacing is not required, the parameter checking algorithm 203 sets the counter 106 and jumps to the second pacing algorithm 204 which is shown in block 302. If pacing is required, for patient safety, but not requested by the second pacing algorithm 204, the first pacing algorithm 202 generates pacing parameters 303 and supplies them through the output I/O unit 110 to the pacing circuit 112 which is shown in block 304.

The first pacing algorithm 202 may be called by the parameter checking algorithm 203 through ordinary process calls well known in the computer art for generating pacing parameters for a specific situation where the second pacing algorithm 204 fails. The first pacing algorithm 202 may as an alternative be called regularly each time the parameter checking algorithm 203 is activated, and is thus always prepared to deliver pacing parameters if needed. The first pacing algorithm 202 may, in addition, generate criteria for use by the parameter checking algorithm 203 for checking the parameters generated by the second algorithm 204.

The parameter checking algorithm 203 then sets the counter 106 and jumps to the second algorithm 204. The counter 106 may be set so that the checking algorithm 203 starts execution every 1–10 ms, i.e. with a frequency between 100 and 1000 Hz.

If the second pacing algorithm 204 has requested pacing, that is, data is stored in the data communication area 205, the data are checked against specific criteria. In the present preferred embodiment a check 305 that a new pacing rate is within a specific range is performed, i.e., it is checked that the new rate is not lower than a minimum rate value and not greater than a maximum rate value. A check 306 for changes in the slope of rate change is performed, i.e., it is checked that a decrease in rate slope is not above a maximum rate slope decrease value, and that an increase in rate slope is not above a maximum rate slope increase value. Also stimulation pulse timing is performed 307, to insure that the stimulation pulse is not in the vulnerable phase of the T-wave. Other criteria can also be used, such as control of whether the duration and amplitude of a stimulation pulse are within given values. The values for the criteria may be set in hardware, or may be set by a medically trained person for a specific patient by telemetry, or can be calculated by the first pacing algorithm 202.

If all criteria are met the pacing parameters generated by the second pacing algorithm 204 are supplied to the pacing circuit 112 through the output I/O unit 110 as shown in block 304. If, however, any of the criteria is not met, the first pacing algorithm generates pacing parameters 303 which are supplied to the pacing circuit 112 through the output I/O unit 110 as shown in block 304.

Figure 4:
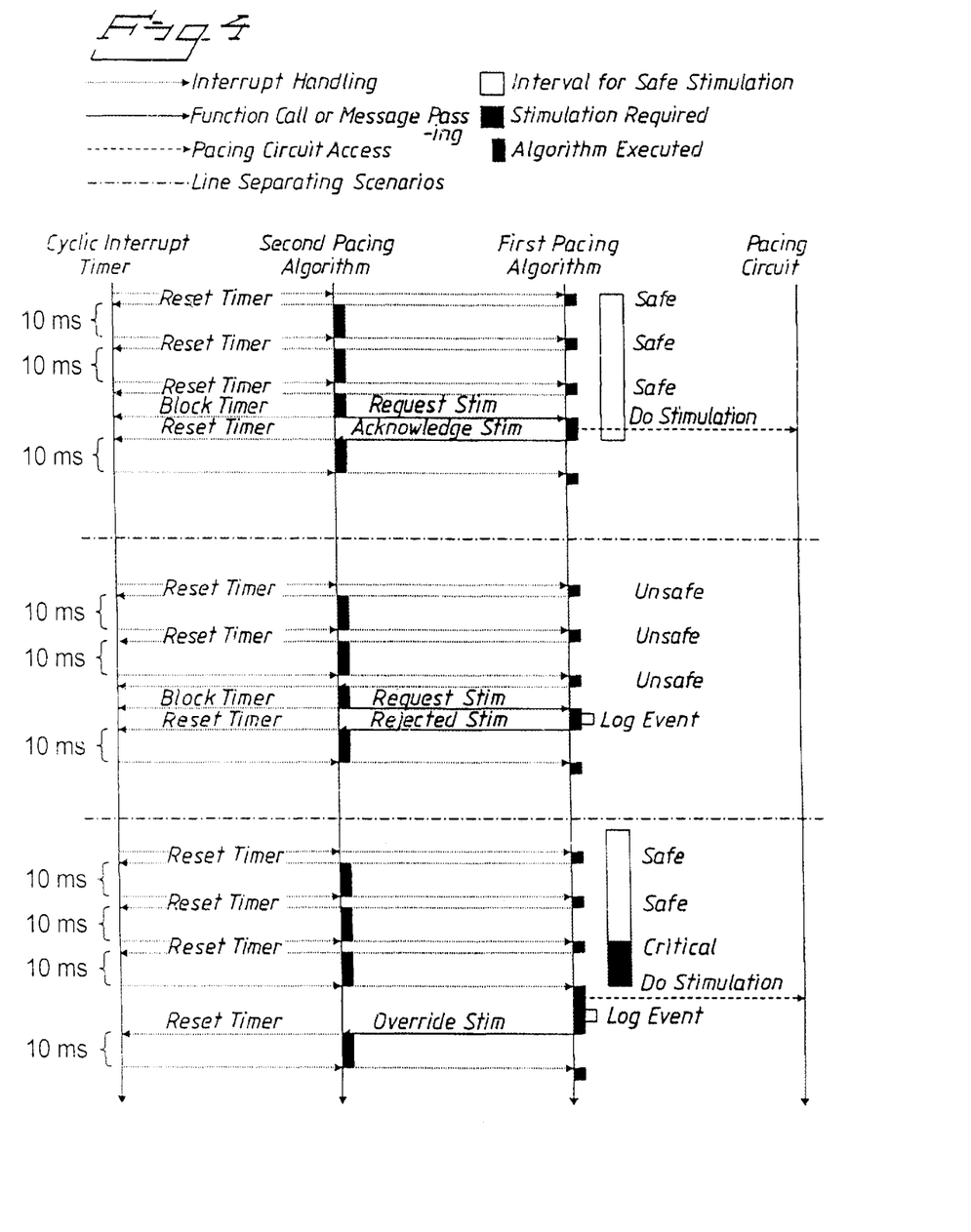
FIG. 4 is a simplified time diagram illustrating the cooperation between the first and second algorithms in the first embodiment of the invention.

FIG. 4 shows a simplified time diagram illustrating the cooperation between the first algorithm 202 and the second algorithm 204 according to the first embodiment of the invention. Three different scenarios are described.

It should be noted that in the illustration of the first embodiment in FIG. 4 the pacing therapy is exemplified by the generation of a stimulation pulse. However, the pacing therapy could of course also include the use of data detected by physiological sensors, involve various changes of the mode of operation for the stimulation device, i.e. mode-switch, involve changes of the amplitude and duration for the stimulation pulse, or enable the stimulation device to detect various heart diseases, e.g. ischemia.

The first scenario can be seen in the upper part of FIG. 4. The left vertical line shows the function of the counter 106, which cyclically generates interrupts. Every $10^{th}$ ms (this time is optional) an interrupt is generated which results in an interruption of the execution of the second pacing algorithm 204 and instead the first pacing algorithm 202 is executed (for some ms. The timer is then reset and the 10 ms period is restarted and the second pacing algorithm is executed again.

When the second pacing algorithm 204 requests a stimulation, a "request stim" is generated and the pacing parameters generated by the second algorithm 204 are checked by the parameter checking algorithm 203. The unfilled box just beside the vertical line illustrating the activity of the first pacing algorithm 202 indicates that pacing is allowed. If the pacing parameters are allowed for stimulation therapy a "do stimulation" is generated to the pacing circuit 112. When the stimulation is performed it is acknowledged by the second pacing algorithm 204.

The second scenario (middle part of FIG. 4) illustrates a situation where a requested stimulation not is allowed (no unfilled box) and the request is rejected and the event (request not allowed) is logged in the memory 102.

The third scenario (lower part of FIG. 4) illustrates a situation where no request for stimulation is generated by the second pacing algorithm 204 but a stimulation is required (black box) by the parameter checking algorithm 203. In this situation the pacing parameters generated by the first pacing algorithm 202 are used to perform the stimulation and to generate the "do stimulation" to the pacing circuit 112.

An important feature of the invention illustrated by FIG. 4 is that both pacing algorithms 202 and 204 are actively generating (updating) their pacing parameters during each heart cycle. This is controlled by the interrupts preferably generated each $10^{th}$ ms. The time for a normal heart cycle is about 1 second (1000 ms).

Figure 5:
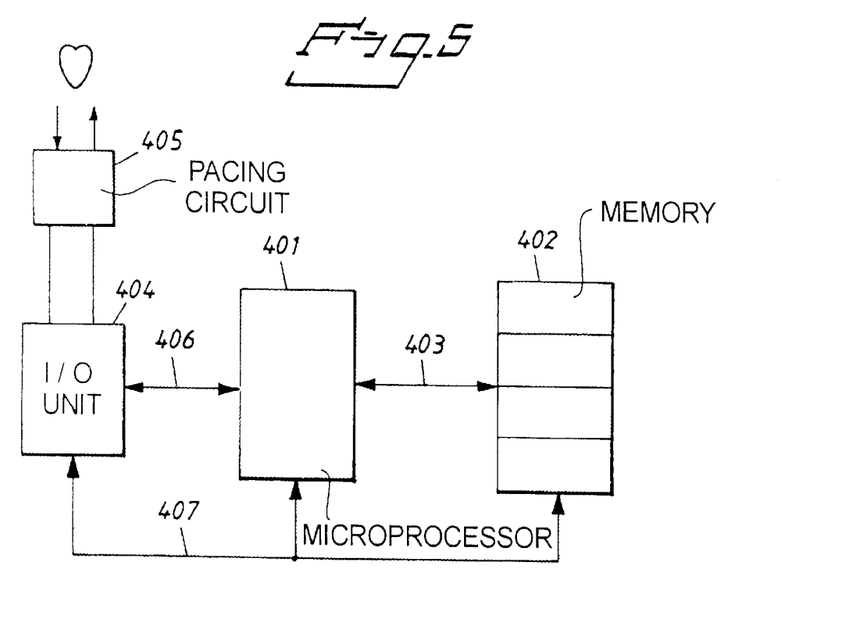
FIG. 5 is a block diagram showing a second embodiment of the invention.

Most microprocessors used in modem computers have support for a supervisor and user mode. A second preferred embodiment of the invention is shown in FIG. 5, using a microprocessor 401 with hardware support for a supervisor and user mode. A memory is denoted 402 and a memory address-bus is denoted 403. An input/output (I/O) unit is denoted 404 and a pacing circuit is denoted 405. An I/O-bus is denoted 406 and a data-bus is denoted 407. The microprocessor 401 has hardware support for a BASE and LIMIT mechanism. The BASE address and LIMIT address are stored in two registers in the microprocessor 401 and may only be changed when the processor 401 is in the supervisor mode. The BASE address contains the lowest memory address which may be used without causing a failure and the LIMIT address contains the highest memory address that may be used without causing a failure.

Figure 6:
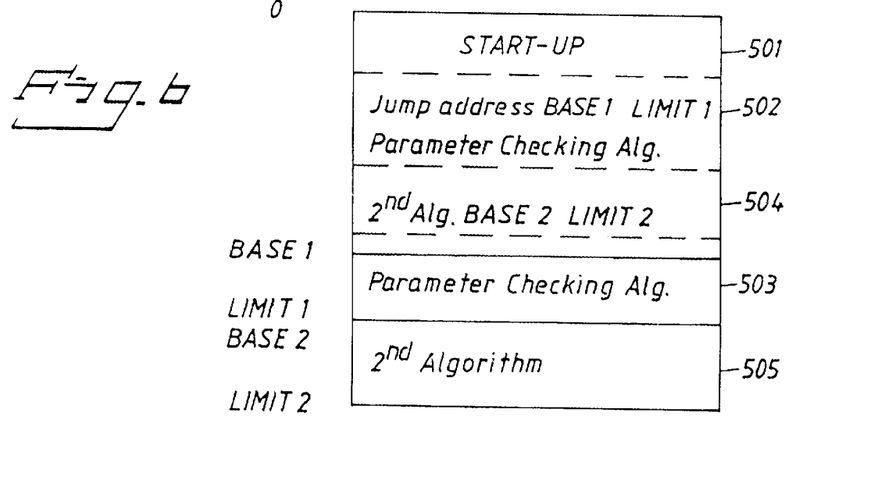
FIG. 6 shows a memory layout for the second embodiment of the invention.

In FIG. 6 a memory layout of the second preferred embodiment is shown. When the microprocessor 401 is restarted a start-up program is executed in the supervisor mode 501. The start-up program contains a jump-table, which is used to jump to different processes and to set the BASE and LIMIT values accordingly. A jump-address 502 is a jump-address to a parameter checking algorithm 503 with BASE address set to BASE1 and LIMIT address set to LIMIT1. A jump-address 504 is a jump-address to a second pacing algorithm 505 with BASE address set to BASE2 and LIMIT address set to LIMIT2.

The second pacing algorithm 505 might be, as indicated above, an advanced pacing algorithm. The parameter checking algorithm 503 performs a number of services and functions similar to an operating system in a modem computer. The parameter checking algorithm 503 provides I/O services to the second pacing algorithm 505 and checks the pacing parameters supplied by the second pacing algorithm 505 in the same way as described above. It has unlimited access to the hardware of the pacemaker and within BASE1 and LIMIT1 is a memory area for memory mapped I/O located. It is thus impossible for the second pacing algorithm 505 to access critical hardware functions. The second pacing algorithm 505 may however have access to signals detected by different kinds of sensors such as accelerometers and pressure sensors.

When the start-up program 501 is finished with the initialization it calls the parameter checking algorithm 503 and sets the appropriate BASE- and LIMIT-addresses. The parameter checking algorithm 503 will initialize and save its state and start execution of the second pacing algorithm 505 after it has set an interrupt timer. If the second pacing algorithm 505 not does return the execution the interrupt timer will ensure that execution is returned to the parameter checking algorithm 503.

All services performed by the parameter checking algorithm 503, such as delivering stimulation pulses are requested by a TRAP signal from the second pacing algorithm 505. Before the TRAP is requested the address of the specific service and the data associated with the service are stored in the registers of the microprocessor 401. If a TRAP has occurred the parameter checking algorithm 503 will examine the supplied data and execute the requested service if it is safe. Any incorrect use of services or memory by the second pacing algorithm 505 will cause a hardware TRAP signal to the parameter checking algorithm 503 which will reset the second pacing algorithm 505.

In this embodiment only one advanced pacing algorithm is shown. It is however possible to have additional concurrent advanced pacing algorithms.

It is also possible to have a first pacing algorithm as a self-contained process and not, as is indicated in this preferred embodiment, as an integrated part of the parameter checking algorithm 503.

Figure 7:
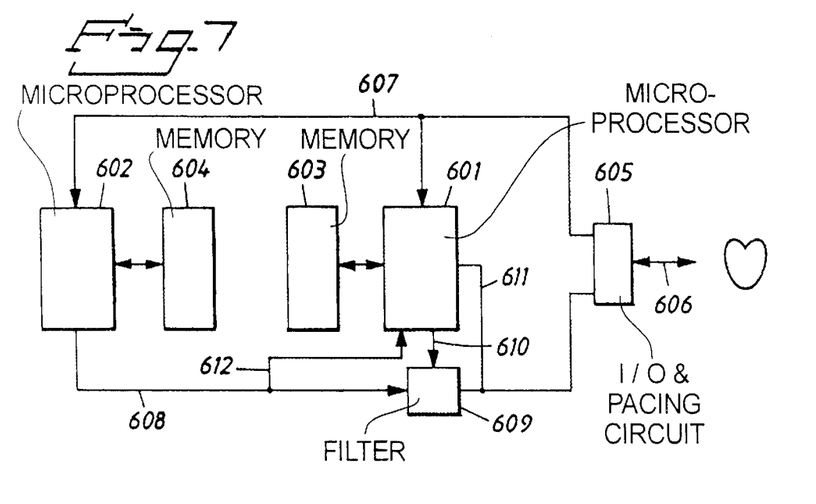
FIG. 7 is a block diagram of a third embodiment of the invention.

FIG. 7 is a block diagram of a third embodiment of the invention where two microprocessors are used, namely a first microprocessor 601 and a second microprocessor 602. A first memory 603 and a second memory 604 are connected to said first and second microprocessors 601 and 602, respectively. An integrated I/O and pacing circuit 605 is connected to an electrode lead 606 to a patient's heart. A connection 607 is connected to the first and second microprocessors 601 and 602 and to the I/O and pacing circuit 605 for applying data representing detected physiological and physical information to a first pacing algorithm and parameter checking algorithm executive in the first microprocessor 601, and to a second pacing algorithm executive in the second microprocessor 602. The first pacing algorithm and the second pacing algorithm are as defined above.

The second pacing algorithm generates pacing parameters to the I/O and pacing circuit 605 via a connection 608 connected to a filter 609. The filter 609 is controlled by the parameter checking algorithm executed in the first processor 601 through a connection 610. The parameter checking algorithm can thus control whether the second pacing algorithm is allowed to send pacing parameters to the I/O and pacing circuit 605. Connection 611 enables the first pacing algorithm to generate pacing parameters to the I/O and pacing circuit 605 if required.

In this third embodiment each of the two microprocessors 601 and 602 is executing a pacing algorithm, and an obvious further embodiment of the invention is to provide more than two microprocessors with each of the microprocessors executing a pacing algorithm.

Figure 8:
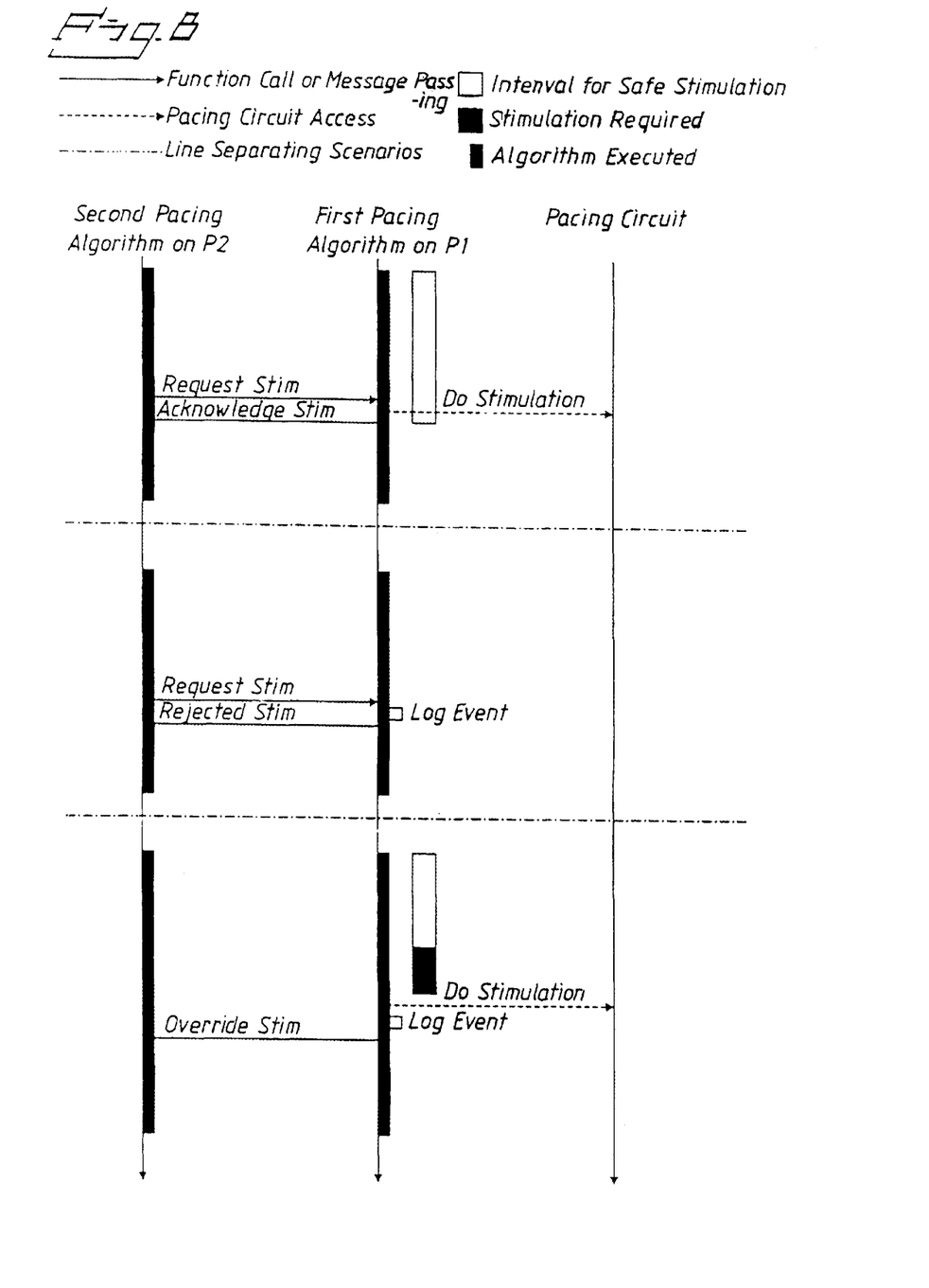
FIG. 8 is a simplified time diagram illustrating the cooperation between the first and second algorithms according to the third embodiment of the invention.

FIG. 8 shows a simplified time diagram illustrating the cooperation between the first and the second algorithms according to the third embodiment of the invention. Three different scenarios are shown.

Compared to the first embodiment of the invention no counter is needed to generate interrupts to switch between the algorithms, instead the two microprocessors 601 and 602 are used, both actively executing a pacing algorithm at the same time.

As shown in the upper part of FIG. 8, when the second pacing algorithm requests a stimulation, a "request stim" is generated and the pacing parameters generated by the second algorithm are checked by the parameter checking algorithm. The unfilled box just beside the vertical line illustrating the activity of the first pacing algorithm indicates that pacing is allowed. If the pacing parameters are allowed for stimulation therapy a "do stimulation" is generated to the I/O and pacing circuit 605. When the stimulation is performed it is acknowledged to the second pacing algorithm.

The second scenario (middle part of FIG. 8) illustrates a situation where a requested stimulation not is allowed (no unfilled box) and the request is rejected and the event (request not allowed) is logged in the memory.

The third scenario (lower part of FIG. 8) illustrates a situation where no request for stimulation is generated by the second pacing algorithm but a stimulation is required (black box) by the parameter checking algorithm. In this situation the pacing parameters generated by the first pacing algorithm are used to perform the stimulation and to generate the "do stimulation" to the I/O and pacing circuit 605. The event (stimulation required but not requested by the second pacing algorithm) is logged in the memory and the second algorithm is signaled ("override stim") that a "do stimulation" is generated by the first algorithm.

Figure 9:
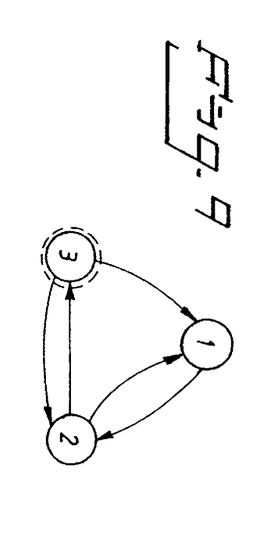
FIG. 9 is a state-diagram for the third embodiment of the invention.

In FIG. 9 a state diagram is shown for the states that the first pacing algorithm and parameter checking algorithm can take.

State 1 is a "prohibit state" in which the filter 609 is blocked. When the parameter checking algorithm is in this state, the second pacing algorithm is prohibited from sending pacing parameters to the I/O and pacing circuit 605 since the filter 609 is blocked. State 2 is an "allowed state" in which the filter 609 is open. Thus, any pacing parameters generated by the second pacing algorithm in the second microprocessor 602 are fed to the I/O and pacing circuit 605. State 3 is a "required state" in which the first algorithm will generate pacing parameters to the I/O and pacing circuit 605. This state is taken when the second pacing algorithm has not generated stimuli within a required time and pacing is required for patient safety. The parameter checking algorithm may take state 1 or state 2 for a specific time, dependent on different criteria similar to those described earlier. For instance, the state taken during the vulnerable phase in the T-wave will be state 1. Through a connection 612 data can be collected by the parameter checking algorithm if pacing is required during a non-allowed state for later analysis.

Figure 10:
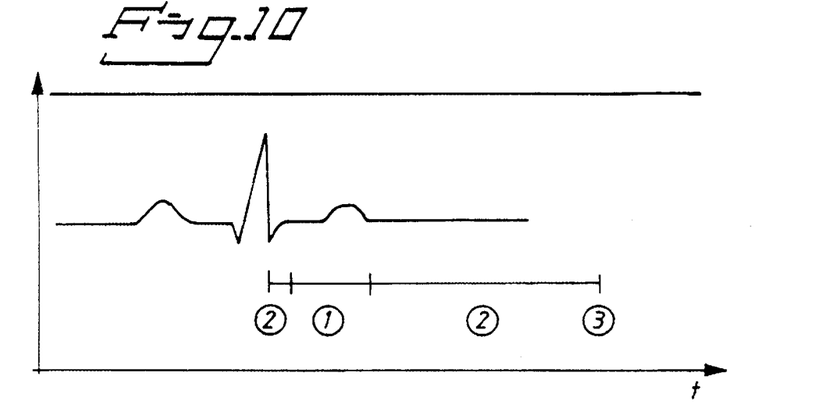
FIG. 10 schematically illustrates an electrocardiogram showing the state transitions indicated in FIG. 9.

FIG. 10 shows an electrocardiogram of a single spontaneous heartbeat and the states taken by the parameter checking algorithm. It should be noted that the different states described in connection with FIG. 10 also are applicable for stimulated heartbeats.

Directly after the QRS the parameter checking algorithm is in state 2 and thus is pacing allowed by pacing parameters generated by the second pacing algorithm. During the vulnerable phase of the T-wave state 1 is taken and thus pacing not allowed by pacing parameters generated by the second pacing algorithm. After the T-wave, pacing is again allowed for a specific time. If no pacing has occurred within this time the parameter checking algorithm will go to state 3 and order the first pacing algorithm to generate pacing parameters to the I/O and pacing circuit 605. The intervals for each state may be set in hardware, or can be set by a medically trained person by telemetry, or are preferably generated by the first pacing algorithm and fed to the parameter checking algorithm.

Thus, when a change of state occurs the parameter checking algorithm jumps to the first pacing algorithm, which calculates the maximum time spent in this state and determines which state to go to next. A number of different events may trigger a state transition, for instance, a spontaneous heart beat, a heart beat triggered by the first or second pacing algorithm, a time-out of a timer set for a specific state, change in a physiological or physical parameter, etc.

The state transitions shown in FIG. 10 are of course only a simple example and considerable transitions that are more complex may occur in more complex pacing algorithms.

Although modifications and changes may be suggested by those skilled in the art, it is in the intention of the inventors to embody within the patent warranted hereon all changes and modifications as reasonably and properly come within the scope of their contribution to the art.

We claim:

1. An implantable cardiac stimulation device comprising:

a stimulation administration arrangement, adapted for interaction with a patient, for administering physiological stimulation to the patient;

a memory arrangement in which a first stimulation algorithm and a second stimulation algorithm are stored; and a microprocessor arrangement having access to said memory arrangement and connected to said stimulation administration arrangement, said microprocessor arrangement executing said first stimulation algorithm to generate stimulation parameters in each heart cycle of said patient and to calculate permissible ranges respectively for said stimulation parameters, and executing said second stimulation algorithm to generate further stimulation parameters in each heart cycle of said patient, said microprocessor controlling said stimulation administration arrangement to administer said physiological stimulation using said stimulation parameters generated by executing said first stimulation algorithm, and to instead, under predetermined conditions, administer said physiological stimulation using said stimulation parameters generated by executing said second stimulation algorithm, said predetermined conditions including a requirement that said further stimulation parameters generated by said second stimulation algorithm are within said parameter ranges.

2. An implantable cardiac stimulation device as claimed in claim 1, wherein, if said further stimulation parameters generated by executing said second stimulation algorithm are not within said parameter ranges, said microprocessor arrangement continues to control said stimulation administration arrangement to administer said physiological stimulation using said parameters generated by executing said first stimulation algorithm.

3. An implantable cardiac stimulation device as claimed in claim 1, wherein said stimulation administration arrangement includes a pulse generating circuit which generates at least one stimulation pulse as said physiological stimulation.

4. An implantable cardiac stimulation device as claimed in claim 3, wherein said pulse generating circuit generates a plurality of pacing pulses as said physiological stimulation.

5. An implantable cardiac stimulation device as claimed in claim 3, wherein said stimulation administration arrangement further comprises an input/output unit connected to said pulse generating circuit and to said microprocessor arrangement, said microprocessor arrangement writing said stimulation parameters into said input/output unit only when executing said first stimulation algorithm.

6. An implantable cardiac stimulation device as claimed in claim 1, wherein said stimulation parameters generated by executing said first stimulation algorithm represent a first stimulation therapy mode and wherein said further pacing parameters generated by executing said second stimulation algorithm represent a second stimulation therapy mode, and wherein said microprocessor arrangement, when executing said first stimulation therapy algorithm, determines, as one of said predetermined conditions, whether a switch should be made from said first stimulation therapy mode to said second stimulation therapy mode.

7. An implantable cardiac stimulation device as claimed in claim 1, wherein said microprocessor arrangement calculates a time window as one of said parameter ranges wherein, if no request to administer said physiological stimulation using said second stimulation algorithm occurs within said time window, said microprocessor arrangement controls said stimulation administration arrangement to administer said physiological stimulation according to said first stimulation algorithm.

8. An implantable cardiac stimulation device as claimed in claim 1, wherein said microprocessor arrangement comprises a single microprocessor for executing both of said first stimulation algorithm and said second stimulation algorithm.

9. An implantable cardiac stimulation device as claimed in claim 1, wherein said microprocessor arrangement comprises a first microprocessor which executes said first stimulation algorithm and a second microprocessor which executes said second stimulation algorithm.

10. An implantable cardiac stimulation device as claimed in claim 9, wherein said first stimulation algorithm includes a parameter checking algorithm, and wherein said second stimulation algorithm supplies said further stimulation parameters to said stimulation administration arrangement through a filter controlled by said parameter checking algorithm.

11. An implantable cardiac stimulation device as claimed in claim 9, further comprising at least one additional microprocessor for executing at least one additional stimulation algorithm stored in said memory arrangement.

* * * * *